United States Patent [19]

Rudolph et al.

[11] Patent Number: 5,284,981

[45] Date of Patent: Feb. 8, 1994

[54] ION EXCHANGERS MODIFIED WITH MERCAPTO AMINES

[75] Inventors: Udo Rudolph; Norbert Bachem; Claus Wulff, all of Krefeld, Fed. Rep. of Germany

[73] Assignee: Bayer Aktiengesellschaft, Leverkusen, Fed. Rep. of Germany

[21] Appl. No.: 517,435

[22] Filed: May 1, 1990

Related U.S. Application Data

[60] Continuation of Ser. No. 122,322, Nov. 18, 1987, abandoned, which is a division of Ser. No. 55,292, May 29, 1987, abandoned.

[30] Foreign Application Priority Data

Jun. 10, 1986 [DE] Fed. Rep. of Germany ....... 3619450

[51] Int. Cl.$^5$ ............................................. C07C 39/12
[52] U.S. Cl. ...................................... 568/727; 521/32
[58] Field of Search ........................... 568/727; 521/32

[56] References Cited

U.S. PATENT DOCUMENTS

| | | | |
|---|---|---|---|
| 3,394,089 | 7/1968 | McNutt et al. | 521/32 |
| 4,346,247 | 8/1982 | Faler et al. | 568/728 |
| 4,369,293 | 1/1983 | Heydenreich et al. | 568/727 |
| 4,595,704 | 6/1986 | Fazio | 521/31 |

*Primary Examiner*—Thurman K. Page
*Assistant Examiner*—Peter F. Kulkosky
*Attorney, Agent, or Firm*—Connolly & Hutz

[57] ABSTRACT

This invention relates to a catalyst modified with mercapto amines, its preparation and its use for the preparation of bisphenols.

3 Claims, No Drawings

ION EXCHANGERS MODIFIED WITH MERCAPTO AMINES

This application is a continuation, of application Ser. No. 07/122,322, filed Nov. 18, 1987, now abandoned, which is a divisional of Ser. No. 055,292, filed May 29, 1987, abandoned.

The condensation of phenols and carbonyl compounds to produce bisphenols is known. A wide variety of catalysts has already been used for this reaction: for example, hydrochloric acid (US-PS 2 182 308 and 2 191 831), boron trifluoride (Chemical Abstracts 58, 3338 c), perchloric acid (Chemical Abstracts 60, 1626 h). benzene sulphonic acid (Chemical Abstracts 59, 511 h) and various cation exchanger resins (e.g. GB-PS 842 209, 849 565 and 883 391). The addition of compounds containing sulphur to the catalyst is also known, e.g. the use of thioglycollic acid and 3-mercaptopropionic acid has been disclosed in U.S. Pat. No. 2 468 982 and 2 623 908, the addition of thiophenols in U.S. Pat. No. 2 359 242. the addition of alkylmercaptans in U.S. Pat. No. 2 775 620 and the addition of hydrogen sulphide in Chemical Abstracts 58. 1403 e.

These known catalysts containing sulphur give rise to considerable damage by corrosion in industrial practice. Bisphenols prepared with the aid of these catalysts are contaminated crude products which contain unreacted phenol, carbonyl compounds, water of reaction and undesirable by-products in addition to bisphenol. Bisphenol A synthesized with these catalysts, for example, contains isomers of bisphenol A, in particular 2,2-(2,4'-dihydroxydiphenyl)-propane and 2,2-(2,2'-dihydroxydiphenyl)-propane complex products such as the so-called "codimer", 2,2,4-trimethyl-4-p-hydroxyphenylchroman, condensation products such as triphenol or even higher condensation products in the form of tarry or high boiling substances as well as decomposition products and substances containing sulphur. The presence of these by-products is undesirable as they tend to remain in the end product and give rise to discolouration. This impairs the usefulness of the end product even when a high degree of purity is not required. In addition, the by-products present interfere with some of the usual reactions of bisphenol, in particular its further reaction to polycarbonates.

U.S. Pat. No. 3 394 089 describes a process for the preparation of bisphenol A from acetone and phenol with the aid of a catalyst containing sulphonic acid groups in which 5 to 25 mols-% of the sulphonic acid groups are blocked with mercapto amines to form ammonium salts which are said to obviate these disadvantages. This modified ion exchanger resin which is obtained by neutralization in aqueous solution, for example with β-mercaptoethylamine, is unsuitable for the production process because it is unstable and because the mercapto compound is washed out by the reaction medium in the course of time so that the catalyst loses its effect.

It has now been found that highly pure bisphenols may be prepared with the aid of highly acid ion exchangers in which the acid groups are neutralized to a very high degree, even quantitatively, this neutralization being carried out on a previously dried ion exchanger in an anhydrous medium.

The present invention relates to a process for the preparation of anhydrous ion exchangers modified with mercapto amines, characterised in that known acid ion exchanger resins which have a total capacity of acid functions of from 0.7 to 2.1 mval/ml of ion exchanger when they have a water content of about 75 to 85% by weight or a total capacity of acid functions of from 3.5 to 5 mval or higher, based on 1 g of dry substance of ion exchanger, are dried and then rinsed with the phenol required for the preparation of the bisphenol and are then neutralized with at least 0.3 mol. preferably with 0.4 to 1 mol of mercapto amines of formula (I) per mol of acid function of the ion exchanger at temperatures above the melting point of this phenol.

The present invention also relates to the ion exchangers modified with mercapto amines of formula (I) obtainable by the process according to the invention.

The acid functions of these modified ion exchangers are occupied with the mercapto amine of formula (I) to an extent of at least 30 mol-% and preferably 40 to 100 mol-%.

Suitable acid ion exchangers include, for example, the conventional reaction products of styrene-divinyl benzene copolymers with conventional sulphonating agents such as sulphuric acid, chlorosulphonic acid etc. These may be present in spherical form with particle diameters of 0.3 to 1.5 mm. They may be of the gel type or macroporous. Their total capacity of acid functions ranges from 0.7 to 2.1 mval/ml of ion exchanger when they are moistened with a water content of about 75 to 85% by weight or from 3.5 to 5 mval or higher, based on 1 g of the dry substance of ion exchanger.

Before the treatment or neutralization with the mercapto amines corresponding to formula (I) which are to be used according to the invention, these ion exchangers are dried, optionally by heat, optionally in a vacuum or optionally by washing with hydrophilic organic liquids such as alcohols or phenols or by azeotropic distillation with organic liquids such as toluene, xylene, methylene chloride or others. The ion exchanger resin is then rinsed with the phenol required for the preparation of the bisphenol, and the required quantity of mercapto amine of formula (I) is then added in this medium at temperatures above the melting point of the phenol with stirring or in a fluidized bed layer.

In the mercapto amines corresponding to formula (I)

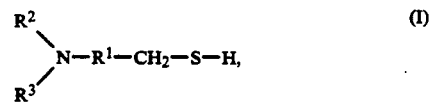

$R^1$ denotes a $C_1$–$C_6$-alkylene, $C_5$–$C_{10}$-cycloalkylene or $C_6$–$C_{14}$-arylene group. preferably a methylene group, and $R^2$ and $R^3$, which are independent of one another. denote $C_1$–$C_6$-alkyl groups or, preferably, hydrogen. The following are suitable mercapto amines corresponding to formula (I): Dimethylmercaptoethylamine. ethyl-cyclohexylmercaptobutylamine, mercaptopropylamine, 1-amino-4-mercaptomethylbenzene and β-mercaptoethylamine; β-mercaptoethylamine is preferred.

The mercapto amines of formula (I) may be used as such or prepared in situ from thiazolidines such as 2,2-dimethyldiazolidine.

The cation exchanger resin which has been modified by neutralization may be used for the preparation of numerous bisphenols from phenols and carbonyl compounds. Suitable phenols include those corresponding to formula (II)

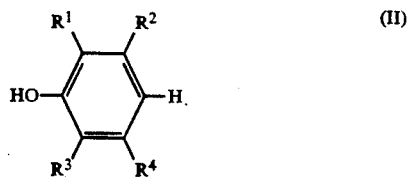

wherein $R^1, R^2, R^3$ and $R^4$ denote, independently of one another, hydrogen (H), $C_1$-$C_4$-alkyl or halogen such as F, Cl or Br.

The following are given as examples: 2,6-Dimethylphenol, o- and m-cresol, o-sec.butylphenol, o-tert.butylphenol, 1,3,5-xylenol, 2,6-ditert.-butylphenol, tetramethylphenol, 2-methyl-6-tert.-butylphenol, o-phenylphenol, o- and m-chlorophenol, o-bromophenol, 6-chloro-o-cresol and 2.6-dichlorophenol.

Unsubstituted phenol is preferred.

Suitable carbonyl compounds include those corresponding to formula (III)

wherein $R^1$ and $R^2$ denote, independently of one another, hydrogen (H), $C_1$-$C_6$-alkyl, $C_6$-$C_{10}$-cycloalkyl, $C_6$-$C_{14}$-aryl, $C_7$-$C_{20}$-aralkyl or $C_7$-$C_{20}$-alkylaryl or $R^1$ and $R^2$ together from a saturated ring with 5 to 6 atoms.

The following are examples of suitable carbonyl compounds such as aldehydes and ketones: Formaldehyde. methyl ethyl ketone, methyl propyl ketone, diethyl ketone, cyclohexanone, acetophenone, etc. Acetone is preferred.

The process of preparation may be carried out continuously or batchwise by methods and with apparatus which are known in the art.

In the batchwise method, 80 to 200 g, preferably 100 to 150 g of dry substance of ion exchanger resin according to the invention are used per mol of carbonyl compound.

The reaction temperature employed for the preparation of the bisphenol is in the region of 40 to 120° C. and is preferably above the solidification point of the components.

The reaction time or dwell time is chosen to be sufficiently long for complete conversion of the carbonyl compound put into the process and is preferably from 30 to 240 minutes.

The present invention accordingly also relates to the use of the ion exchangers modified with mercapto amines of formula (I) obtained by the process according to the invention for the preparation of bisphenols from phenols and carbonyl compounds.

The reaction mixture obtained from the reaction of phenol with carbonyl compound is worked up by the usual methods such as distillation, crystallisation, etc.

Thus, for example, the bisphenol prepared may be cooled in the reaction mixture until crystallisation sets in and the phenol may then be removed by distillation or extraction from the mixed crystals of bisphenol and phenol which have been filtered off.

The bisphenol prepared by this process is suitable for known fields of application without after-purification and is also suitable for applications in which an exceptionally high standard of purity is required, such as the preparation of optically highly pure polycarbonates.

EXAMPLE 1

Preparation of the Modified Ion Exchanger Resin

The water-moist ion exchanger as obtained from the supplier with a moisture content of about 80% by weight and a total capacity of 0.75 mval/ml is washed with distilled water. It is then dried for 24 hours in a water jet vacuum at 90 to 100° C. to reduce the water content to below 1% by weight.

The remaining water is distilled off as an azeotropic mixture with toluene and the toluene adhering to the ion exchange resin is then distilled off in a water jet vacuum at 95° C.

120 g of this pretreated ion exchanger resin are taken up with 1128 g of phenol in a stirrer apparatus and left to swell in the phenol at 65° C. for 24 hours with exclusion of moisture. The quantity of mercapto ethylamine required for blocking the mol-% indicated in Examples 2 to 10 is then added with stirring.

EXAMPLES 2-10

Preparation of Bisphenol A (BPA)

The ion exchanger resin was modified with β-mercapto ethylamine by the process described in Example 1 so that 15 to 100% of the sulphonic acid groups were neutralised in nine different adjustments. 58 g of acetone were added at 65° C. to the solution prepared in Example 1 and the purity of the bisphenol and quantity of by-products were determined gas chromatographically after complete conversion of the acetone. The results obtained are summarized in the following Table in terms of the mean values obtained in each case from 5 experimental examples.

| Example | Mol-% occupied | GC surface percentages BPA | By-products |
|---|---|---|---|
| 2 | 15 | 93.6 | 6.4 (comparison) |
| 3 | 20 | 93.8 | 6.2 (comparison) |
| 4 | 25 | 94.3 | 5.7 (comparison) |
| 5 | 30 | 94.5 | 5.5 |
| 6 | 40 | 94.7 | 5.3 |
| 7 | 50 | 95.1 | 4.9 |
| 8 | 60 | 95.7 | 4.3 |
| 9 | 80 | 96.2 | 3 B |
| 10 | 100 | 96.7 | 3.3 |

We claim:

1. In the process for producing bisphenols by condensing a phenol with a carbonyl compound in the presence of the catalyst, the improvement comprises said catalyst being an anhydrous ion exchange resin with a total capacity of acid function of from 3.5 to 5 mval per 1 gram of dry ion exchange resin and which has been after drying partially neutralized with at least 0.3 mol of mercapto amines per mol of acid function in a anhydrous medium.

2. The process according to claim 1 wherein the mercapto amine is of the formula (I)

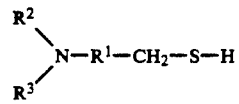

in which $R^1$ is $C_1$-$C_6$ alkylene, $C_5$-$C_{10}$ cycloalkylene or $C_6$-$C_{14}$ arylene and $R^2$ and $R^3$, independently of one another, are $C_1$-$C_6$ alkyl or hydrogen.

3. The process according to claim 1 wherein phenol and acetone are reacted to produce bis-phenol A.

* * * * *